(12) United States Patent
Repine et al.

(10) Patent No.: US 11,376,311 B2
(45) Date of Patent: Jul. 5, 2022

(54) METHODS OF TREATING MICROBIAL INFECTION AND INFLAMMATION

(71) Applicants: COLORADO SEMINARY, OWNER AND OPERATOR OF UNIVERSITY OF DENVER, Denver, CO (US); THE REGENTS OF THE UNIVERSITY OF COLORADO, A BODY CORPORATE, Denver, CO (US)

(72) Inventors: John Repine, Englewood, CO (US); Amani Alhalwani, Jeddah (SA)

(73) Assignees: COLORADO SEMINARY, OWNER AND OPERATOR OF UNIVERSITY OF DENVER, Denver, CO (US); THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 65 days.

(21) Appl. No.: 16/761,215

(22) PCT Filed: Nov. 1, 2018

(86) PCT No.: PCT/US2018/058626
§ 371 (c)(1),
(2) Date: May 1, 2020

(87) PCT Pub. No.: WO2019/089878
PCT Pub. Date: May 9, 2019

(65) Prior Publication Data
US 2020/0261548 A1   Aug. 20, 2020

Related U.S. Application Data

(60) Provisional application No. 62/580,563, filed on Nov. 2, 2017.

(51) Int. Cl.
| | | |
|---|---|---|
| *A61K 31/5513* | (2006.01) | |
| *A61K 31/66* | (2006.01) | |
| *A61K 35/74* | (2015.01) | |
| *A61K 38/40* | (2006.01) | |
| *A61P 31/04* | (2006.01) | |
| *A61K 9/00* | (2006.01) | |
| *A61K 31/4164* | (2006.01) | |

(52) U.S. Cl.
CPC ............ *A61K 38/40* (2013.01); *A61K 9/0048* (2013.01); *A61K 31/4164* (2013.01); *A61P 31/04* (2018.01)

(58) Field of Classification Search
CPC combination set(s) only.
See application file for complete search history.

(56) References Cited

U.S. PATENT DOCUMENTS

| | | |
|---|---|---|
| 2002/0068013 A1 | 6/2002 | Wilcox et al. |
| 2004/0047823 A1 | 3/2004 | Catroux et al. |
| 2006/0263320 A1 | 11/2006 | Bissett |
| 2008/0107603 A1 | 5/2008 | Aruoma |
| 2009/0214431 A1* | 8/2009 | Grundemann ......... C07K 14/47 424/9.2 |
| 2012/0141611 A1 | 6/2012 | Landes et al. |
| 2013/0004651 A1 | 1/2013 | Fu-giles |
| 2013/0079379 A1* | 3/2013 | Shanler .................. A61P 17/06 514/401 |
| 2013/0101575 A1 | 4/2013 | Ashby et al. |
| 2013/0155370 A1 | 6/2013 | Zhang et al. |
| 2016/0338993 A1 | 11/2016 | Martins-green et al. |

OTHER PUBLICATIONS

Barnet products, Thiotaine, accessed Dec. 2, 2021 at URL protecingredia.com/brochure/Thiotaine.pdf (2007) (Year: 2007).*
Gonzalez-Chavez et al, "Lactoferrin: structure, function and applications," International Journal of antimicrobial agents 33:301.e1-e8 (2009) (Year: 2009).*
International Search Report dated Jan. 24, 2019 in International Application No. PCT/US2018/058626 (3 pages).
Wikipedia "Ergothioneine", Version: Jun. 23, 2017 (Jun. 23, 2017), Retrieved: Dec. 17, 2018 (Dec. 17, 2018 (https://en.wikipedia.org/w/index.php?title=Ergothioneine&oldid=787139336) p. 1, para 1 (5 pages).

* cited by examiner

*Primary Examiner* — Julie Ha
*Assistant Examiner* — Kristina M Hellman
(74) *Attorney, Agent, or Firm* — Dorsey & Whitney LLP

(57) ABSTRACT

Methods of treating or preventing microbial infection in a subject in need of treatment by administering a therapeutically effective amount of ergothioneine, or functional analog, or prodrug, or salt thereof. Ergothioneine may be advantageously administered in conjunction with lactoferrin.

12 Claims, 3 Drawing Sheets

METHODS OF TREATING MICROBIAL INFECTION AND INFLAMMATION

CROSS REFERENCE TO RELATED APPLICATION

This application is a national stage application under 35 U.S.C. § 371 of International Application No. PCT/US2018/058626 filed Nov. 1, 2018, which claims the benefit of U.S. Provisional Patent Application Ser. No. 62/580,563, filed Nov. 2, 2017, the entire disclosures of which are incorporated herein by reference.

TECHNICAL FIELD

This invention relates generally to the field of antimicrobial compositions. More particularly, this disclosure relates to methods of treating subjects suffering from bacterial infections by administering to a subject in need of such treatment a therapeutically effective amount of ergothioneine, or salt thereof. The anti-bacterial efficacy may be enhanced by co-administration of the ergothioneine with lactoferrin.

BACKGROUND

Many health conditions are characterized by infection and/or inflammation, including various conditions of the eyes, ears, nose, and throat. While it is often difficult to discern underlying causes, such conditions may be treated with, for example, topical or systemic antibiotics, antivirals, and/or anti-inflammatory agents depending on the suspected etiology. Such treatments are however limited by microbial resistance, drug toxicity, irritation, and/or hypersensitivity that may develop. Methods and compositions for broadly, effectively, and safely treating infected regions and/or inflammatory conditions of the body are needed.

Infections due to multidrug resistant pathogens are increasing worldwide. Their multidrug resistance profile makes currently available therapeutic options extremely limited. Some of these pathogens include methicillin-resistant *Staphylococcus aureus* (MRSA), multidrug-resistant *Streptococcus pneumoniae*, and vancomycin-resistant enterococci (VRE) among the Gram-positive bacteria; and multidrug-resistant *Acinetobacter baumannii*, *Pseudomonas aeruginosa* and Enterobacteriaceae (including *Klebsiella pneumoniae* and *Escherichia cob*), among the Gram-negative bacteria. In view of the rising bacterial resistance rates worldwide, there is an anticipated demand for novel antibiotic compositions to broaden the antimicrobial spectrum, improve the efficacy, prevent the emergence/re-emergence of resistant bacteria, and lower the dose of the individual antibiotic drugs to reduce the side effects as well as the treatment costs.

The development of resistance to antibiotics is well-documented for both Gram-negative bacteria and Gram-positive bacteria, which has implications in the ability to treat infections and diseases that afflict millions of people across the world leading to suffering, economic loss and premature death. In particular, Gram-negative bacteria are more resistant to antibiotics than Gram-positive bacteria due to the presence of an outer membrane, which provides an efficient barrier to both hydrophilic and hydrophobic compounds. Consequently, Gram-negative bacterial infections are typically more problematic to treat in view of the fewer classes of antibiotics available for effective treatment.

As an example, carbapenems possess broad-spectrum activity against many Gram-negative bacteria and remain the 'final-line' drug of choice for extended-spectrum, 3-lactamase-producing organisms. However, the increasing prevalence of carbapenem-resistant and carbapenemase-producing organisms is jeopardizing the efficacy of carbapenems, and carbapenem-resistant "superbugs," which may exhibit broad resistance to many other antibiotic classes, may leave an infection untreatable. Hence, seeking alternative treatment regimens has become a pressing issue.

Similarly, colistin (a 50-year old polymyxin class antibiotic), is undergoing a period of revival, and is favored as a 'last line' therapeutic against these hard to treat multidrug-resistant bacteria, such as *P. aeruginosa*, *A. baumannii* and *K. pneumoniae*. Unfortunately, in recent years, sporadic reports of colistin-resistant strains have even started emerging in Singapore, Greece, Israel and South Korea.

Combination antibiotic regimens are attractive alternative strategies to overcoming these rising rates of drug resistance in the dearth of newer antibiotics. These combinations are useful in eradicating pathogens and the simultaneous use of multiple classes of antibiotics is also useful in protecting against the re-emergence of drug resistant bacteria.

As such, there is considerable interest in developing more effective treatments for infection and/or inflammation.

SUMMARY

The present disclosure provides compositions that are active against the growth or persistence of bacteria present within the body or cells of another organism, e.g. a plant or animal. The invention thus provides a broadly effective and safe treatment for conditions characterized by infection (bacterial, viral, or fungal), and/or inflammation (including acute and chronic inflammation, as well as delayed-type and immediate-type hypersensitivity), to avoid development of bacterial resistance to antibiotics, and to avoid toxicity, irritation, and/or hypersensitivity that may occur with conventional agents.

In one aspect, the present disclosure provides methods of treating an infection in a subject in need of treatment thereof. The method includes administering to the subject a therapeutically effective amount of at least one compound, wherein the at least one compound is at least ergothioneine (ERGO; 3-(2-Sulfanylidene-1,3-dihydroimidazol-4-yl)-2-(trimethylazaniumyl)propanoate). Preferably, the ERGO is the L isomer (i.e., L-Ergothioneine). The ERGO may be L-Ergothioneine, a precursor of ERGO, a salt thereof, or a biologically active analog, and/or prodrug thereof.

The ERGO may be administered with another agent, or agents, effective in preventing or treating an infection, including bacterial, viral, protozoan, and fungal infections. The other agent may include lactoferrin (LF; lactotransferrin (LTF)). The LF may be a precursor of LF, a salt thereof, or a biologically active analog, and/or prodrug thereof. In these methods, the ERGO may enhance the anti-microbial activities of LF.

A subject receiving treatment for a microbial infection pursuant to the methods of this disclosure may have an infection of a bacterial, viral, protozoal, and/or fungal source. In these methods, the subject may be experiencing an inflammatory condition secondary to the microbial infection. In such instances, the inflammatory condition may be effectively treated or ameliorated by the administration of the ERGO or ERGO in combination with other agents. In these methods, the microbial infection may be an infection of the skin, eye, ear, nose, mouth, or throat. In these methods, the microbial infection may be an antibiotic-resistant bacterial infection. For example, the bacterial infection may be resistant to a beta-lactam or fluoroquinolone antibiotics. In these methods, the ERGO may be administered after an unsuccessful (ineffective) antibiotic treatment. In these methods, the ERGO may be administered in place of an antibiotic treatment or prior to an antibiotic treatment, such as a LF treatment. In these methods, the infectious and/or inflammatory condition may be chronic or recurring. In these methods, the treatment may reduce the capacity of the infection to spread. In these methods, the infection may be an acute infection. In these methods, the ERGO may be administered instead of anti-inflammatory medication and/or antibiotics, and the ERGO may reduce inflammation and/or effectively treat the infection.

This disclosure also provides a composition comprising ERGO and another anti-microbial and/or anti-inflammatory agent, and optionally one or more excipients in a pharmaceutical carrier for the treatment of a condition related to microbial infections or inflammation. In these compositions, the ERGO may comprise at least 50% (w/v) of the composition. In these compositions, the ERGO may comprise at least 90% (w/v) of the composition. In these compositions, the other agent may be molecules such as small molecule antibiotics, natural or synthetic peptide antimicrobials, or proteins with antimicrobial properties, or a combination thereof. In these compositions, the other agent may be lactoferrin, and in such compositions, the lactoferrin may comprise at least 50% (w/v) of the composition. In these compositions, the lactoferrin may comprise at least 90% (w/v) of the composition.

This Summary is neither intended nor should it be construed as being representative of the full extent and scope of the present invention. Moreover, references made herein to "the present disclosure," or aspects thereof, should be understood to mean certain embodiments of the present invention and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary.

Additional aspects of the present disclosure will become more readily apparent from the Description of Embodiments, particularly when taken together with the drawings.

DETAILED DESCRIPTION

Figure 1A:
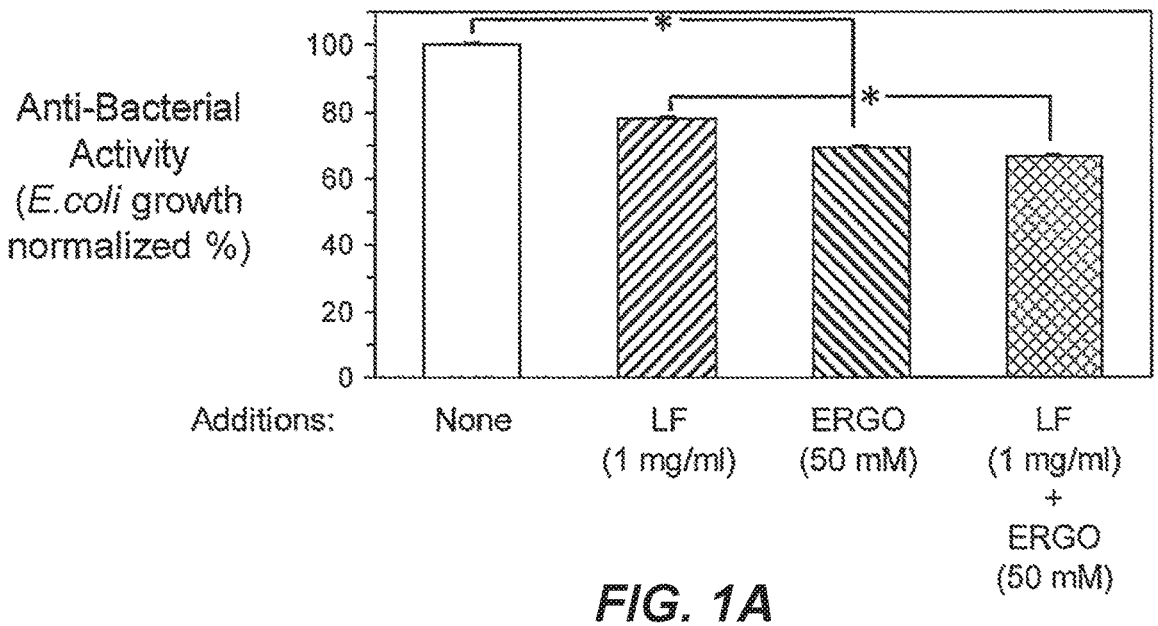
FIGS. 1A and 1B show the antibacterial effects of several concentrations of ERGO and ERGO+LF on *E. coli*. Each value is the mean+/−standard error of the mean (SEM) of 4 or more individual determinations.
Figure 1B:
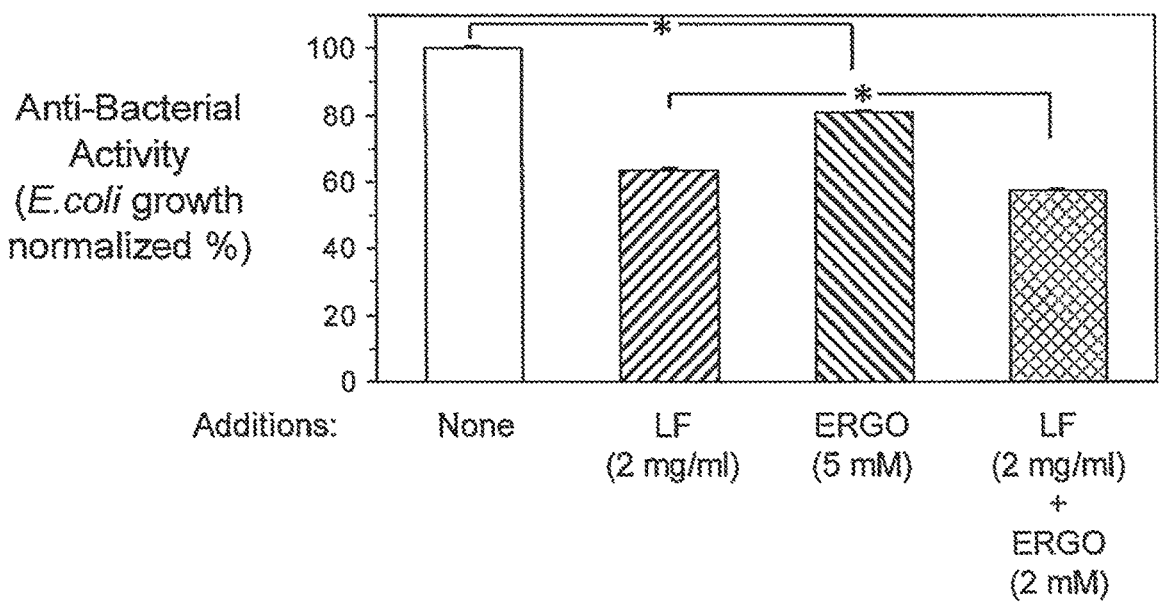
Figure 2:
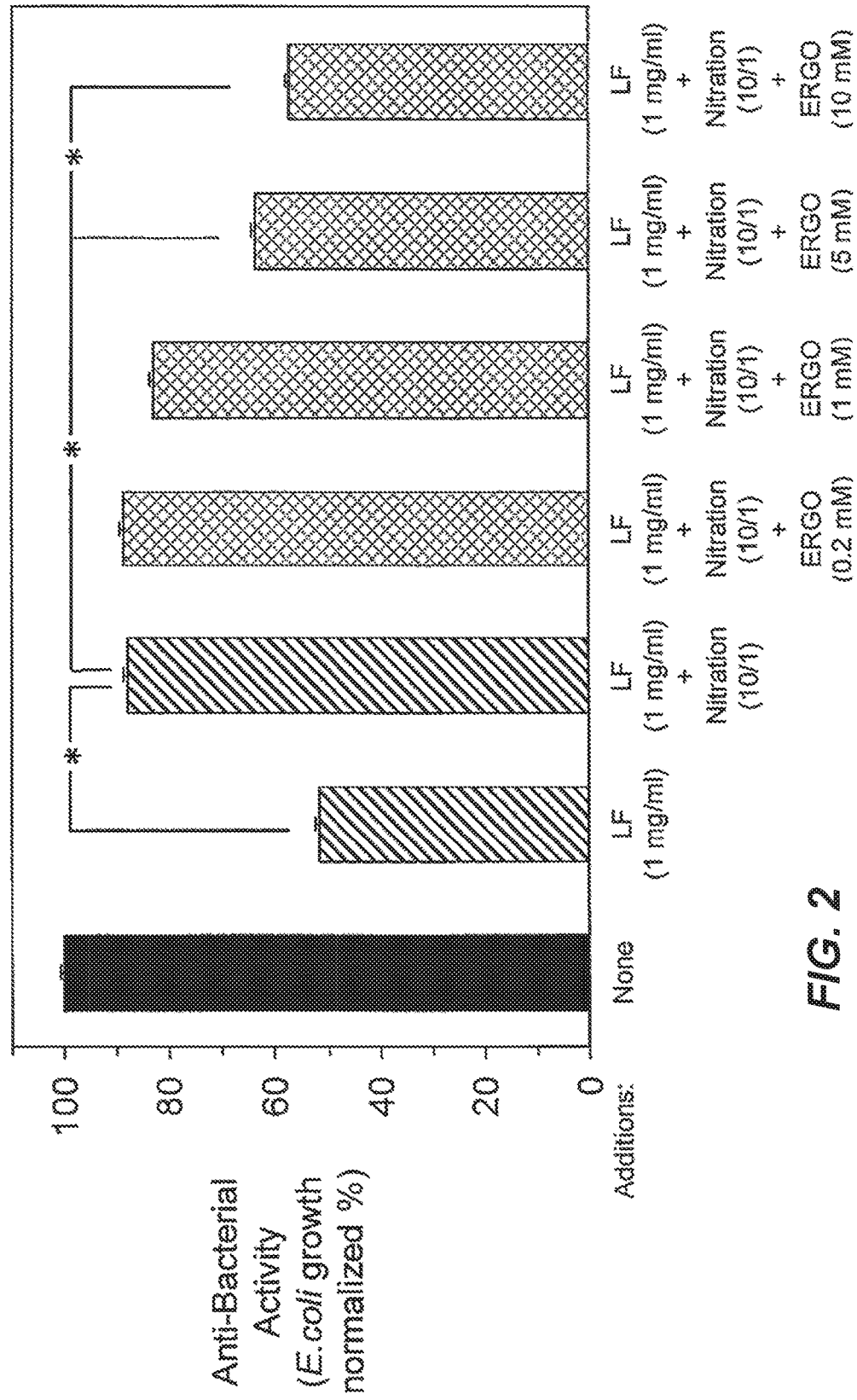
FIG. 2 shows the effects of various concentrations of ERGO on the anti-bacterial activity of LF exposed to nitrating agents. Each value is the mean+/−standard error of the mean (SEM) for 4 or more individual determinations.
Figure 3:
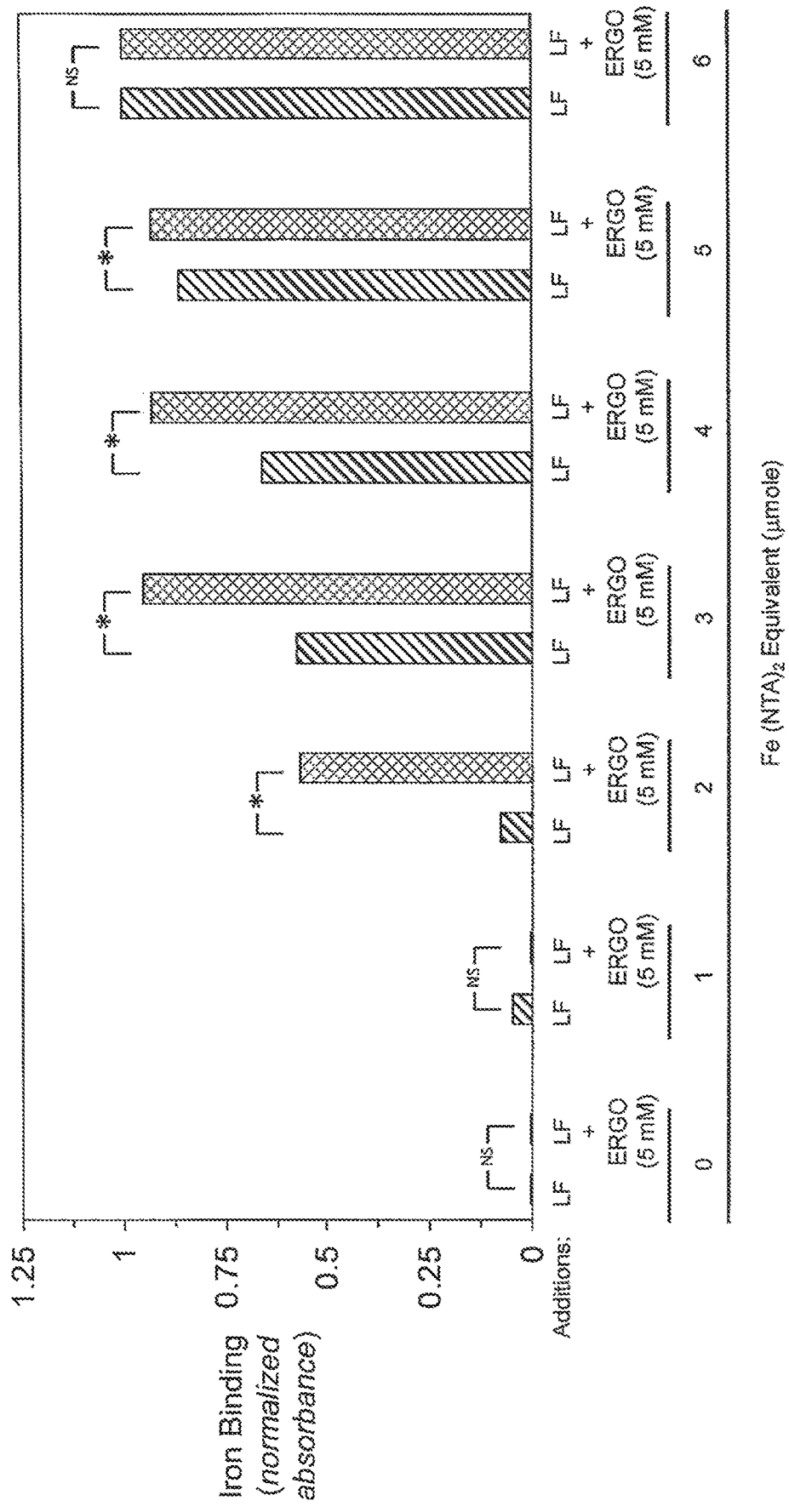
FIG. 3 shows the effect of ERGO on the ferrous iron (Fe++) binding capacity of LF.

This disclosure provides methods for treating infections and inflammatory conditions in a subject in need of such treatment. In addition, the present disclosure also relates to methods of preventing the spread or progression of a microbial infection, methods of decreasing inflammation in a subject, methods of preventing inflammation in a subject, and methods of reducing or reversing microbial organism count in or on a biological tissue. These methods will generally comprise administering to a subject in need of such therapy a therapeutically- or prophylactically-effective amount of at least ergothioneine (ERGO), or a biologically active analog and/or prodrug thereof, or salt thereof, to the subject.

Definitions

The terms "administer", "administering", "administered" or "administration" refer to any manner of providing a drug (such as ERGO and/or LF) to a subject or patient. Routes of administration can be accomplished through any means known by those skilled in the art. Such means include, but are not limited to, oral, topical, buccal, intravenous, subcutaneous, intramuscular, intradermal, or intrathecal administration, by implantation, or as part of a medical or personal care device, and the like.

As used herein, the term ergothioneine (ERGO) refers to the naturally-occurring amino acid having the chemical structure:

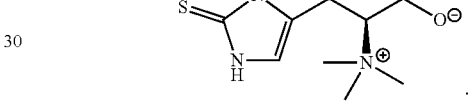

L-ergothioneine is an intracellular antioxidant found in plants and animals, but not synthesized in human bodies; it comes only from dietary sources. The antioxidant properties of ergothioneine appear to be related to its ability to scavenge reactive oxygen species (free radicals), chelate various metallic cations, activate antioxidant enzymes such as glutathione peroxidase ($SeGP_x$) and manganese superoxide dismutase (Mn SOD) and to inhibit superoxide-generating enzymes such as NADPH-Cytochrome C reductase, and to affect the oxidation of various hemoproteins such as hemoglobin and myoglobin. Additionally, ergothioneine prevents or reduces nitration of biological molecules (Arduini, A., "Possible Mechanism of Inhibition of Nitrite-Induced Oxidation of Oxyhemoglobin by Ergothioneine and Uric Acid," Arch. Biochem. Biophys., 294(2):398-402 (May 1992)). ERGO is made in relatively few organisms, notably Actinobacteria, Cyanobacteria, and certain fungi. ERGO is available commercially in purified form. In humans, ergothioneine is acquired exclusively through the diet and accumulates in erythrocytes, bone marrow, liver, kidney, seminal fluid and eyes. Ergothioneine absorption and accumulation requires a specific transporter, OCTN1, to enter cells. The metabolic pathway to produce ergothioneine starts with the methylation of histidine to produce histidine betaine (hercynine). The sulfur atom is then incorporated from cysteine. The biosynthetic genes of ergothioneine have been described in *Mycobacterium smegmatis, Neurospora crassa,* and *Schizosaccharomyces pombe*.

As used herein, an "infection" is used as it is in the art, and includes bacterial, fungal, viral, and protozoal infections as well as disorders, conditions or symptoms associated with the infection, including inflammatory conditions. The infection can be in any system, organ, tissue or area of the subject, such as but not limited to, gastrointestinal, urinary, skin, ocular, auditory, blood, and respiratory to name a few.

As used herein, the phrase "reducing infection" or "reducing microbial organism count" in a subject refers to reduction of the number of microbial organisms or reduction of microbial growth responsible for the infected state in the subject upon intake of ERGO according to the methods of this disclosure. Any amount of microbial organism elimination or growth reduction is acceptable, as long as it is reduced by a statistically significant amount.

As used herein, the term "pharmaceutically acceptable" includes moieties or compounds that are, within the scope of sound medical judgment, suitable for use in contact with the tissues of humans and lower animals without undue toxicity, irritation, allergic response, and the like, and are commensurate with a reasonable benefit/risk ratio.

As used herein, the term "subject" refers to an animal, preferably a mammal, including a human or non-human. The terms "patient" and "individual" and "subject" may be used interchangeably herein.

The terms "therapeutically effective amount" or "prophylactically effective amount" of a drug (namely, ERGO, or a salt thereof) refers to a nontoxic but sufficient amount of the drug to provide the desired effect. The amount of drug that is "effective" or "prophylactic" will vary from subject to subject, depending on the age and general condition of the individual, the particular drug or drugs that may be co-administered with ERGO, and the like. Thus, it is not always possible to specify an exact "therapeutically effective amount" or a "prophylactically effective amount." However, an appropriate "therapeutically effective amount" or "prophylactically effective amount" in any individual case may be determined by one of ordinary skill in the art.

The terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual by inhibiting or causing regression of a disorder or disease.

As used herein, the term "prodrug" refers to a derivative of ERGO compounds that have chemically- or metabolically-cleavable groups and become by solvolysis or under physiological conditions compounds that are pharmaceutically active in vivo. Esters of carboxylic acids are an example of prodrugs that can be used in the dosage forms of the present disclosure.

Methods of Treatment

As described above, this disclosure provides methods of treating or preventing infections in a subject as well as treating or preventing inflammatory conditions that arise from such infections.

The methods of this disclosure involve establishing the presence of a microbial infection in a subject and administering ERGO to the subject in need of such anti-microbial treatment(s). Once a subject has been determined to be suffering from an infection, or if a subject has been exposed to a microbial source, the subject can be administered a therapeutically effective amount of ERGO, thereby treating the infection in the subject.

The ERGO may be ingested one time per day, two times per day, three times per day (e.g., around each meal), four times per day, or more during the treatment period. The dosage may be provided in a single unit dosage form (e.g., a single pill, capsule or tablet) or may be provided in smaller unit dosage forms if the oral composition is intended to be taken more than once per day.

The treatment period is ideally of sufficient time for the ERGO to provide an improvement in the infection and/or underlying inflammatory condition. The treatment period may be at least 2 days, preferably at least 4 days, more preferably at least 6 days, or 8 days, or 10 days, or even indefinitely. In some instances, the treatment period will extend over multiple weeks (e.g., 1, 2, 3, 4, 5, 6, 7, 8, 10, 12 or more weeks) or multiple months (e.g., 1, 2, 3, 4, 5 or more months).

After the subject has received administration of ERGO for a specified period of time (such as a day, a week, two weeks, three weeks, four weeks, etc.), a second determination of the presence of the infection or inflammatory condition may be conducted to determine whether the infection has been successfully treated or at least reduced in the subject. Any amount of statistically significant reduction in the infection is encompassed by the methods of the present disclosure.

Moreover, ERGO can be used to further treat or enhance the anti-microbial activity in subjects already receiving one or more anti-microbial compounds. Particularly, the ERGO may be administered in conjunction with lactoferrin. Lactoferrin (LF) is an 80 kDa glycoprotein that exists in mucosal secretions from exocrine glands (milk, colostrum, uterine fluid, vaginal secretion, seminal fluid, saliva, bile, pancreatic juice, small intestine secretions, nasal secretions and tears) and the secondary (specific) and tertiary granules of neutrophils. LF is produced during neutrophil differentiation and then dispersed when mature neutrophils release their granules ("degranulation"). This process is associated with the process of phagocytosis. Phagocytosis is defined by attachment and engulfment processes that encapsulate bacteria within phagocytic vacuoles where the bacteria are then attacked and damaged by toxic free radicals generated by NADPH oxidase, a component of the neutrophil membrane, and neutrophil granular products like LF that are discharged into the phagocytic vacuole. Intracellular killing of bacteria by neutrophils depends on the optimal interactions of both free radical generation and degranulation. Neutrophil degranulation is also the main source of LF in the blood. LF is also produced by kidneys. LF exists in all biological fluids but its concentrations are highest at sites of infection and inflammation. LF has many functions including the ability to bind ferrous iron (Fe++) and control iron distribution throughout the body, and the ability to bind to inflammatory and other cell membranes and impact the activities of these cells through this and other mechanisms. LF is appreciated as a contributor to the innate immune system but the mechanisms by which it contributes remain unclear and apparently vary depending on the microorganism and the surrounding conditions. LF has antimicrobial functions that can limit the growth of bacteria, viruses, protozoa and fungi. The antibacterial, antiviral, and antiparasitic activity may or may not be connected to its iron binding ability. For some bacteria, LF may have a bacteriostatic effect by binding free iron but, in contrast, LF can also serve as an iron donor and support bacterial growth. The antibacterial properties of LF have also been linked to its ability to prevent bacterial biofilm formation, provide iron that enhances intracellular free radical formation by neutrophils, generate bacteria killing proteolytic activity, electrostatic interactions that disrupt bacterial cell walls (Baveye, S., et al.; "Lactoferrin: a multifunctional glycoprotein involved in the modulation of the inflammatory process" Clinical Chemistry and Laboratory Medicine 37 (3): 281-286 (1999)). The antiviral activity of LF may be a result of its ability to bind certain DNA and RNA viruses; the antiparasitic activity of LF may be related to its ability to damage the membranes of parasites (Van der Strate, B. W. A., et al.; "Antiviral activities of lactoferrin." Antiviral research 52(3): 225-239 (2001). LF suggested to be a potential therapeutic for human medical condition with no side effect after metabolized. (Weinberg, Eugene D. "Human lactoferrin: a novel therapeutic with broad spectrum potential." Journal of Pharmacy and Pharmacology 53(10): 1303-1310 (2001).

Thus, the ERGO can be used as a monotherapy or as part of a combination therapy in treating or decreasing microbial infection and inflammation in a subject. Compounds or compositions comprising ERGO may be administered in combination with at least one other agent effective in reducing infection or inflammation. Such other agent may be selected from an antibiotic, and antifungal, an antiviral, an antiprotozoal therapy, and/or an anti-inflammatory, as would be understood by one skilled in the art.

Air pollution, from sources such as the combustion of solid fuels and tobacco smoking, often causes ocular irritation. The components of such air pollution that are irritating to the eyes include Carbon dioxide, Carbon monoxide (CO), Sulfur oxides ($SO_X$), Nitrogen oxides ($NO_X$), Volatile organic compounds (VOC), particulate matter (PM), atmospheric particulate matter (i.e., fine particles, are tiny particles of solid or liquid suspended in a gas), free radicals connected to airborne fine particles, Chlorofluorocarbons, Ammonia, and combinations thereof.

In areas with elevated levels of such pollution, a significant proportion of residents report their eyes were always irritated, and these areas show elevated levels of cataract, Age Related Macular Degeneration (AMD), Dry Eye Disease (DED), Dry Eye Syndrome (DES), infectious eye diseases including repeated re-infections with *Chlamydia trachomatis*, corneal infections and corneal ulcers. The co-occurrence in developing countries of exposure to household fuel combustion products and higher rates of blindness, especially in females, makes it imperative to find solutions that can protect against the irritation and eye damage caused by air pollution.

DES and related diseases can be caused by environmental conditions, such as the pollution described above, as well as autoimmune conditions and/or any activity that decreases the rate of blinking, and/or by decreased tear production or a change in tear composition that results in inadequate lubrication of the eye. Contact lens use, eye surgery, and eye injury can also induce DES. Finally, DES often occurs as a consequence of aging and hormonal changes.

All of these sources of eye irritation may cause symptoms of discomfort, visual disturbance, and tear film instability, with potential damage to the ocular surface, and inflammation of the ocular surface. Signs or symptoms of such eye irritation may include dry, scratchy, stingy, itchy, burning or pressured sensations, irritation, pain, redness, inflammation, discharge, and excessive eye watering.

Thus, one aspect of this disclosure provides methods for reducing, diminishing or ameliorating irritation to an eye or to a skin region surrounding the eye, by topically administering to the eye or to the skin region surrounding the eye a formulation comprising ergothioneine (ERGO), a precursor of ERGO, a salt thereof, or a biologically active analog, or prodrug thereof. These methods may include the topical administration of lactoferrin (LF), a precursor of LF, a salt thereof, or a biologically active analog, or prodrug thereof, which may be administered simultaneously with, or as part of a single composition comprising, the ergothioneine.

Thus, in a related aspect, this disclosure provides a formulation comprising ERGO, or a combination of ERGO and LF, the formulation being capable of reducing, diminishing or ameliorating irritation to an eye. Such formulation is a topical pharmaceutical or cosmetic composition, preferably prepared as eye drops, but may also be supplied, for example, as an eye ointment or medicated contact. In these methods, the topical formulations are effective to reduce, or ameliorate irritation of mucous membranes of the eye including irritation of mucous membranes of the eye caused by at least one of allergies, chemical pollutants, and physical irritants.

Therapeutic Compositions

Compositions containing ERGO in combination with at least one other pharmaceutical compound are contemplated for use in the methods of this disclosure. Such other pharmaceutical compound may be selected from an antibiotic, and antifungal, an antiviral, an antiprotozoal therapy, and/or an anti-inflammatory compound. Such other pharmaceutical compound may be lactoferrin. Using the excipients and dosage forms described below, formulations containing such combinations are a matter of choice for those skilled in the art. Further, those skilled in the art will recognize that various coatings or other separation techniques may be used in cases where the combination of compounds are incompatible.

The ERGO compounds of this disclosure may also be present in the form of pharmaceutically acceptable salts. For use in medicine, the salts of the compounds of this disclosure refer to non-toxic "pharmaceutically acceptable salts" (see, International J. Pharm., 1986, 33, 201-217; J. Pharm. Sci., 1997 (January), 66, 1, 1). Other salts may, however, be useful in the preparation of ERGO according to this disclosure or of its pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

Basic addition salts can be prepared in situ during the final isolation and purification of compounds by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

ERGO or salts thereof, may be formulated in a variety of ways that is largely a matter of choice depending upon the delivery route desired. For example, solid dosage forms for oral administration include capsules, tablets, pills, powders and granules. In such solid dosage forms, these compounds may be mixed with at least one inert, pharmaceutically acceptable excipient or carrier, such as sodium citrate or dicalcium phosphate and/or a) fillers or extenders, such as, but not limited to, starches, lactose, sucrose, glucose, mannitol and silicic acid; b) binders, such as, but not limited to, carboxymethylcellulose, alginates, gelatin, polyvinylpyrrolidone, sucrose and acacia; c) humectants, such as, but not limited to glycerol; d) disintegrating agents, such as, but not limited to, agar-agar, calcium carbonate, potato or tapioca starch, alginic acid, certain silicates and sodium carbonate; e) solution retarding agents, such as, but not limited to, paraffin; f) absorption accelerators, such as, but not limited to, quaternary ammonium compounds; g) wetting agents, such as, but not limited to, cetyl alcohol and glycerol monostearate; h) absorbents, such as, but not limited to, kaolin and bentonite clay; and i) lubricants, such as, but not limited to, talc, calcium stearate, magnesium stearate, solid polyethylene glycols, sodium lauryl sulfate and mixtures thereof.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

Liquid dosage forms for oral administration include pharmaceutically acceptable emulsions, solutions, suspensions, syrups and elixirs. In addition to the ERGO, the liquid dosage forms may contain inert diluents commonly used in the art such as, for example, water or other solvents, solubilizing agents and emulsifiers, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

The compositions can also be delivered through a catheter for local delivery at a target site, via an intracoronary stent (a tubular device composed of a fine wire mesh), or via a biodegradable polymer, or personal care items, such as a contact lens.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include, but are not limited to, water, ethanol, polyols (propylene glycol, polyethylene glycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form can be brought about by the use of agents delaying absorption, for example, aluminum monostearate and gelatin.

Suspensions, in addition to the active compounds (i.e., ERGO and LF or salts thereof), may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Proper fluidity can be maintained, for example, by the use of coating materials such as lecithin, by the maintenance of the required particle size in the case of dispersions and by the use of surfactants.

In some cases, in order to prolong the effect of the ERGO or salts thereof and accompanying therapeutic agent(s), it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Dosage forms for topical administration of the compounds of this present disclosure include powders, sprays, ointments and inhalants. The active compound(s) is mixed under sterile conditions with a pharmaceutically acceptable carrier and any needed preservatives, buffers or propellants which can be required. Opthalmic formulations, eye ointments, powders and solutions are also contemplated within the scope of this disclosure.

Topical pharmaceutical or cosmetic compositions for administration to the eye or regions surrounding the eye may include one at least one substance selected from the group consisting of pharmaceutically acceptable excipients; pharmaceutically acceptable additives; and pharmaceutically acceptable preservatives. These formulations may also include at least one viscosity enhancing agent, such as hydroxypropylcellulose. These formulations may also include at least one surface active agent that can decrease the surface tension of the solution thereby increasing the spread of the solution over the mucus membranes of the eye. In some preferred embodiments of the invention, these topical formulations may comprise at least one viscosity enhancing agent in a concentration that yields a viscosity of between 5 and 100 centipose (cP). Preferably these topical formulations are formulated as aqueous eye drop compositions.

Exemplary compounds incorporated to facilitate and expedite transdermal delivery of topical compositions into ocular or adnexal tissues include, but are not limited to, alcohol (ethanol, propanol, and nonanol), fatty alcohol (lauryl alcohol), fatty acid (valeric acid, caproic acid and capric acid), fatty acid ester (isopropyl myristate and isopropyl n-hexanoate), alkyl ester (ethyl acetate and butyl acetate), polyol (propylene glycol, propanedione and hexanetriol), sulfoxide (dimethylsulfoxide and decylmethylsulfoxide), amide (urea, dimethylacetamide and pyrrolidone derivatives), surfactant (sodium lauryl sulfate, cetyltrimethylammonium bromide, polaxamers, spans, tweens, bile salts and lecithin), terpene (d-limonene, alpha-terpeneol, 1,8-cineole and menthone), and alkanone (N-heptane and N-nonane). Moreover, topically-administered compositions may comprise surface adhesion molecule modulating agents including, but not limited to, a cadherin antagonist, a selectin antagonist, and an integrin antagonist.

Optionally, the composition further contains a compound selected from the group consisting of a physiological acceptable salt, poloxamer analogs with carbopol, carbopol/hydroxypropyl methyl cellulose (HPMC), carbopol-methyl cellulose, carboxymethylcellulose (CMC), hyaluronic acid, cyclodextrin, and petroleum.

These compositions may be formulated as an ointment, a gel, a liquid, an aerosol, a mist, a polymer, a contact lens, a film, an emulsion, or a suspension.

When formulated as a contact lens, the ERGO and/or LF are incorporated into or coated onto the lens. The composition is chemically bound or physically entrapped by the contact lens polymer. Alternatively, a color additive is chemically bound or physically entrapped by the polymer composition that is released at the same rate as the therapeutic drug composition, such that changes in the intensity of the color additive indicate changes in the amount or dose of therapeutic drug composition remaining bound or entrapped within the polymer. Alternatively, or in addition, an ultraviolet (UV) absorber is chemically bound or physically entrapped within the contact lens polymer. The contact lens is either hydrophobic or hydrophilic.

Exemplary materials used to fabricate a hydrophobic lens with means to deliver the compositions of this disclosure include, but are not limited to, amefocon A, amsilfocon A, aquilafocon A, arfocon A, cabufocon A, cabufocon B, carbosilfocon A, crilfocon A, crilfocon B, dimefocon A, enflufocon A, enflofocon B, erifocon A, flurofocon A, flusilfocon A, flusilfocon B, flusilfocon C, flusilfocon D, flusilfocon E, hexafocon A, hofocon A, hybufocon A, itabisfluorofocon A, itafluorofocon A, itafocon A, itafocon B, kolfocon A, kolfocon B, kolfocon C, kolfocon D, lotifocon A, lotifocon B, lotifocon C, melafocon A, migafocon A, nefocon A, nefocon B, nefocon C, onsifocon A, oprifocon A, oxyfluflocon A, paflufocon B, paflufocon C, paflufocon D, paflufocon E, paflufocon F, pasifocon A, pasifocon B, pasifocon C, pasifocon D, pasifocon E, pemufocon A, porofocon A, porofocon B, roflufocon A, roflufocon B, roflufocon C, roflufocon D, roflufocon E, rosilfocon A, satafocon A, siflufocon A, silafocon A, sterafocon A, sulfocon A, sulfocon B, telafocon A, tisilfocon A, tolofocon A, trifocon A, unifocon A, vinafocon A, and wilofocon A.

Exemplary materials used to fabricate a hydrophilic lens with means to deliver the compositions of this disclosure include, but are not limited to, abafilcon A, acofilcon A, acofilcon B, acquafilcon A, alofilcon A, alphafilcon A, amfilcon A, astifilcon A, atlafilcon A, balafilcon A, bisfilcon A, bufilcon A, comfilcon A, crofilcon A, cyclofilcon A, darfilcon A, deltafilcon A, deltafilcon B, dimefilcon A, droxfilcon A, elastofilcon A, epsilfilcon A, esterifilcon A, etafilcon A, focofilcon A, galyfilcon A, genfilcon A, govafilcon A, hefilcon A, hefilcon B, hefilcon C, hilafilcon A, hilafilcon B, hioxifilcon A, hioxifilcon B, hioxifilcon C, hydrofilcon A, lenefilcon A, licryfilcon A, licryfilcon B, lidofilcon A, lidofilcon B, lotrafilcon A, lotrafilcon B, mafilcon A, mesafilcon A, methafilcon B, mipafilcon A, nelfilcon A, netrafilcon A, ocufilcon A, ocufilcon B, C, ocufilcon D, ocufilcon E, ofilcon A, omafilcon A, oxyfilcon A, pentafilcon A, perfilcon A, pevafilcon A, phemfilcon A, polymacon, senofilcon A, silafilcon A, siloxyfilcon A, surfilcon A, tefilcon A, tetrafilcon A, trilfilcon A, vifilcon A, vifilcon B, and xylofilcon A.

It will be understood that formulations used in accordance with the methods of the present disclosure generally will comprise a therapeutically effective amount of ERGO. The phrase "therapeutically effective amount" or "prophylactically effective amount" as used herein means a sufficient amount of, for example, ERGO, or formulation necessary to treat the infection, at a reasonable benefit/risk ratio applicable to any medical treatment. As with other pharmaceuticals, it will be understood that the total daily usage of a pharmaceutical composition of the disclosure will be decided by a medical professional within the scope of sound medical judgment. The specific therapeutically effective or prophylactically effective dosage level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and other factors known to those of ordinary skill in the medical arts. For example, it is well within the skill of the art to start doses of the compound at levels lower than required to achieve the desired therapeutic effect and to gradually increase the dosage until the desired effect is achieved.

Formulations of the present disclosure are administered and dosed in accordance with sound medical practice, taking into account the clinical condition of the individual patient, the site and method of administration, scheduling of administration, and other factors known to medical practitioners.

Therapeutically effective or prophylactically effective amounts for purposes herein thus can readily be determined by such considerations as are known to those skilled in the art. The daily therapeutically effective or prophylactically effective amount of the ERGO administered to a patient in single or divided doses range from about 0.01 to about 750 milligram per kilogram of body weight per day (mg/kg/day).

EXAMPLES

The following methods were used to conduct the experiments described in Examples 1-3, below: The experiments were conducted using the standard broth dilutions susceptibility test (Jorgensen, J. H.; Turnidge, J. D., Susceptibility test methods: dilution and disk diffusion methods. In Manual of Clinical Microbiology, Eleventh Edition, American Society of Microbiology: 2015; pp 1253-73). Briefly, 1 µl of glycerol stock aliquot of $E.\ coli$ (ATCC 25922) was inculcated into Tryptic Soya agar (TSA) (Sigma Aldrich 22091) plates and incubated at 37° C. for 24 hrs. Subsequently, 3-5 separate colonies were selected and transferred into 4 ml Tryptic Soya broth (TSB) (Sigma Aldrich 22092) and incubated at 37° C. for 24 hrs. After incubation, samples were diluted 4 ml into 50 ml TSB to make $E.\ coli$ stock. 200 µl samples were then placed into wells of a 96-microwell plate.

All samples were prepared in TSB, (Blank) using TSB, ERGO (OXIS International), LF (Sigma Aldrich) and NLF were diluted to 1 mg/ml. The nitration reaction was prepared following the method reported by Selzle et al (Determination of nitration degrees for the birch pollen allergen Bet v 1. Analytical and Bioanalytical Chemistry 2013, 405(27): 8945-49). According to this procedure, 400 µl aliquots of 5.0 mg/ml (±5%) LF in aqueous solution were pipetted into glass vials. PBS buffer followed by sodium peroxynitrite was then added to each vial, and reaction solutions were stirred with magnetic bars on ice for 2 hours. Sodium peroxynitrite was added in two different amounts (11.32 µl and 45.46 µl) corresponding to peroxynitrite to tyrosine ($ONOO^-$/Tyr) molar ratios of 10/1 and 40/1. Different volumes of PBS buffer were added to each solution to make a total volume of 1000 µl and producing a NLF concentration of 2 mg/ml (±5%). 200 µl of 2 mg/ml of NLF diluted 1:1 with TSB was used in each well. 5 µl of *E. coli* stock was added to each well and incubated at 37° C. overnight. ERGO or LF were added in various concentrations along with *E. coli*. Finally, the cleared areas on the microwell plates were examined at wavelength 600 nm. Using the plate reader (Tecan Infinite, M1000 PRO).

Example 1

ERGO is Anti-Bacterial and Increases the Anti-Bacterial Activity of Lactoferrin As described above, ERGO is known to have antioxidant properties. Because of its known antioxidant properties, the inventors anticipated that ERGO would protect bacteria against inflammation and oxidative stress by preventing the toxic effect of peroxides, rather than have antimicrobial activity. To test the antimicrobial activity of ERGO, in the presence and absence of LF, the inventors tested two concentrations of ERGO (5 mM or 50 mM) and two concentrations of LF (1 mg/ml or 2 mg/ml) on solutions of *E. coli* using the protocol described above.

Adding LF (1 mg/ml or 2 mg/ml) or ERGO (5 mM or 50 mM) reduced the growth of *E. coli* compared to the growth of *E. coli* without additions (FIGS. 1A and 1B). Similarly, adding ERGO (50 mM or 5 mM) to LF (1 mg/ml or 2 mg/ml, respectively) reduced the growth of *E. coli* compared to the growth of *E. coli* following addition of LF (1 mg/ml or 2 mg/ml, respectively) alone (FIGS. 1A and 1B).

Example 2

ERGO Preserves the Anti-Bacterial Activity of LF Previously Exposed to Nitrating Agents LF is known to have anti-bacterial activity related both to its intrinsic properties and its role as a constituent of neutrophils that are effective killers of bacteria. LF is also known to be susceptible to nitration. The inventors tested the effect of ERGO on nitrating LF using the protocols described above.

Adding previously nitrated LF did not inhibit the growth of *E. coli* as much as adding native (non-nitrated) LF. In contrast, LF to which ERGO was added prior to adding nitrating agents, had increased anti-bacterial activity compared to LF previously subjected to nitrating agents without the addition of ERGO. As shown in FIG. 2, the degree to which the ERGO retains anti-bacterial activity was related to the concentration of ERGO added to the LF composition.

Example 3

ERGO Preservation of the Anti-Bacterial Activity of LF During Exposure to Nitrating Agents does not Involve Alterations in the Ferrous Iron (Fe++) Binding Capacity of LF As noted above, LF binds ferrous iron (Fe++) and controls iron distribution throughout the body and its ability to bind to inflammatory and other cell membranes and impact the activities of these cells through its iron binding activities and other mechanisms. The inventors hypothesized that the antibacterial effect may be linked to the iron binding activity of LF and that this antibacterial effect may be disrupted by nitration.

By subjecting LF to nitration in the presence and absence of ERGO, and measuring the effects on antibacterial activity using the protocols described above, the inventors observed that the iron-binding capacity of LF remained intact following sodium peroxinitrite-induced nitration of the iron-containing form of the protein. However, sodium peroxinitrite caused changes that went far beyond the mere nitration of a few tyrosine residues to include destruction of tyrosine and tryptophan which at least in part were converted to unidentified reaction products. Nitration can occur as a consequence of the formation of reactive nitrogen species in the body and as a result of drug or chemical reactions, and/or environmental toxins in polluted air, water, or other routes of intake.

Importantly, with respect to the present discovery, it does not appear that the ability of ERGO to increase the antibacterial activity of LF results from binding of Fe++ on LF (FIG. 3). This suggests that a unique, previously undefined and unanticipated, mechanism is responsible for the ability of ERGO to enhance and preserve the anti-bacterial activity of LF, both before and after exposure to nitrating agents.

The various features of ERGO and/or LF, and compositions containing them, and methods of administering them, described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. The example method steps may be performed in serial, in parallel, or in some other manner. Method steps may be added to or removed from the disclosed example embodiments. The example methods and compositions and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed is:

1. A method for reducing, diminishing, or ameliorating irritation to, or inflammation of, an eye or to a skin region surrounding the eye, comprising administering to the eye or to the skin region surrounding the eye:
   a therapeutically effective amount of ergothioneine (ERGO), a precursor of ERGO, a salt thereof, or a biologically active analog or prodrug thereof, and
   a therapeutically effective amount of lactoferrin (LF), or a precursor of LF, a salt thereof, or a biologically active analog, or prodrug thereof,
   wherein the ERGO enhances an anti-microbial activity of the LF.

2. A method for reducing, diminishing, or ameliorating irritation to, or inflammation of, an eye or to a skin region surrounding the eye, comprising administering to the eye or to the skin region surrounding the eye:
   a therapeutically effective amount of ergothioneine (ERGO), a precursor of ERGO, a salt thereof, or a biologically active analog or prodrug thereof, and
   a therapeutically effective amount of lactoferrin (LF), or a precursor of LF, a salt thereof, or a biologically active analog, or prodrug thereof,
   wherein the LF has been exposed to a nitrating agent and the ERGO preserves the anti-microbial activity of the LF.

3. The method of claim 1, wherein the eye irritation is associated with exposure of the eye to air pollution.

4. The method of claim 1, wherein the ERGO, precursor of ERGO, salt thereof, or biologically active analog or prodrug thereof is administered topically.

5. The method of claim 1, wherein the LF, precursor of LF, salt thereof, biologically active analog, or prodrug thereof is administered topically.

6. The method of claim 1, wherein the ERGO, precursor of ERGO, salt thereof, or biologically active analog or prodrug thereof, and the LF, precursor of LF, salt thereof, biologically active analog, or prodrug thereof are administered in one or more compositions.

7. The method of claim 1, wherein the ERGO is L-ergothioneine.

8. The method of claim 2, wherein the eye irritation is associated with exposure of the eye to air pollution.

9. The method of claim 2, wherein the ERGO, precursor of ERGO, salt thereof, or biologically active analog or prodrug thereof is administered topically.

10. The method of claim 2, wherein the LF, precursor of LF, salt thereof, biologically active analog, or prodrug thereof is administered topically.

11. The method of claim 2, wherein the ERGO, precursor of ERGO, salt thereof, or biologically active analog or prodrug thereof, and the LF, precursor of LF, salt thereof, biologically active analog, or prodrug thereof are administered in one or more compositions.

12. The method of claim 2, wherein the ERGO is L-ergothioneine.

* * * * *